United States Patent [19]

Deja

[11] Patent Number: 4,580,454
[45] Date of Patent: Apr. 8, 1986

[54] SAMPLING APPARATUS

[75] Inventor: Edmund P. Deja, Vassar, Mich.

[73] Assignee: Holgate Corporation, Saginaw, Mich.

[21] Appl. No.: 619,362

[22] Filed: Jun. 11, 1984

[51] Int. Cl.⁴ .............................................. G01N 1/12
[52] U.S. Cl. .................................................. 73/864.63
[58] Field of Search ........... 73/864.63, 864.64, 864.65, 73/864.66, 864.67

[56] References Cited

U.S. PATENT DOCUMENTS

| 275,694 | 4/1883 | O'Hara . | |
|---|---|---|---|
| 397,961 | 2/1889 | Bergman | 73/864.63 |
| 1,049,153 | 12/1912 | Savino . | |
| 1,210,487 | 1/1917 | Kaul | 73/864.63 |
| 1,785,766 | 12/1930 | Callaway . | |
| 1,857,537 | 5/1932 | Frank et al. | 73/864.63 |
| 2,040,701 | 5/1936 | Marsden | 73/864.63 |
| 2,298,627 | 10/1942 | Proudman | 73/864.63 |
| 3,841,162 | 10/1974 | Duperon | 73/864.67 |

Primary Examiner—Stewart J. Levy
Assistant Examiner—Tom Noland
Attorney, Agent, or Firm—Learman & McCulloch

[57] ABSTRACT

Apparatus for sampling the fluid contents of a container comprising an elongate tube open at one end and having at its other end a cap provided with an air passage. Extending through the tube is an operating rod having a stopper at one end and a valve between its ends. A handle connected to the rod is operable to move the rod between positions in which the opposite ends of the tube are sealed by the stopper and the valve, respectively.

13 Claims, 4 Drawing Figures

U.S. Patent
Apr. 8, 1986
4,580,454
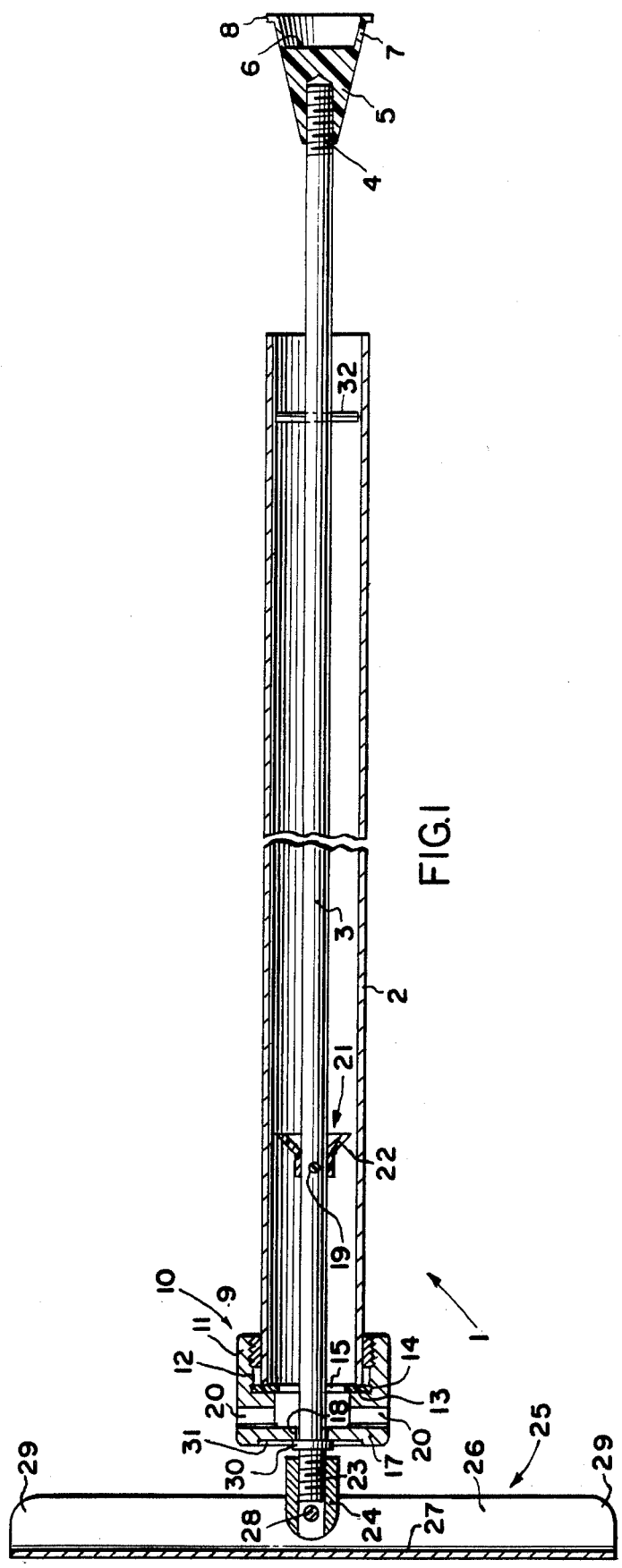
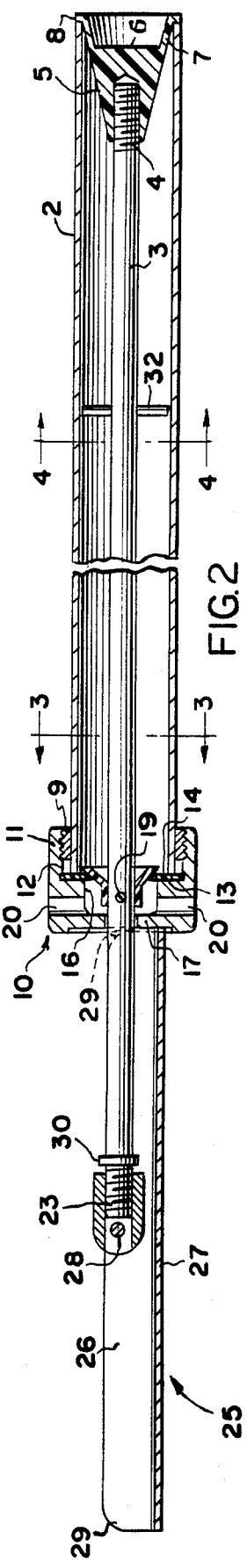
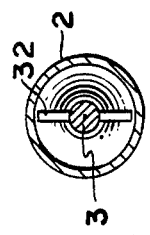
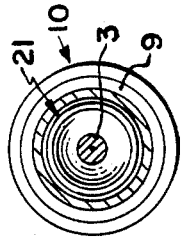

SAMPLING APPARATUS

BACKGROUND OF THE INVENTION

This invention relates to sampling apparatus adapted to be immersed in a fluid for extracting therefrom a sample of a potentially or actually hazardous nature.

There are many occasions when the contents of tanks, drums, and other containers must be subjected to a sampling process to determine the nature of the contents. In many instances the containerized material is known to be of a hazardous nature necessitating the use of special procedures and protective clothing for the sampling personnel, and the manufacture of the sampling apparatus from materials which are essentially inert and relatively unbreakable. These considerations are equally important in those instances in which the nature of the contents of a container is unknown.

The problems associated with the sampling of actually or possibly hazardous materials have been recognized heretofore. For example, the United States Environmental Protection Agency caused a report (EPA-600 2-80-018) entitled *Samplers And Sampling Procedures For Hazardous Waste Streams* to be published in January, 1980. This report discusses the problems involved in the sampling of hazardous materials and traces the development of coliwasas, an acronym for composite liquid waste samplers. Although the coliwasas described in the report have advantages over samplers predating such coliwasas, the coliwasas known heretofore still have disadvantages which apparatus constructed in accordance with the invention disclosed herein overcomes.

One of the most serious disadvantages of hazardous material sampling apparatus heretofore known is the possibility that the sample contained in the sampler may escape therefrom inadvertently and inflict serious injury on the sampling personnel. This possibility is present primarily because it apparently has not been possible heretofore to provide a seal at opposite ends of a sampling tube so as to prevent the discharge of the sample from the tube in the event the tube inadvertently is shifted to some position other than vertical.

Persons taking samples very often have to clamber about on stacked tanks, drums, and the like, which offer uncertain footing at best. As a consequence the sampler often is subjected to violent movements, or is dropped, as the person holding the sampler strives to maintain his or her balance in the transfer of the sample and sampling apparatus from the sampling site to the analysis site. Apparatus constructed in accordance with the invention provides for a much greater resistance to inadvertent spillage of a sample than sampling apparatus heretofore known in use.

SUMMARY OF THE INVENTION

Sampling apparatus constructed in accordance with the preferred embodiment of the invention comprises an elongate tube formed of relatively inert material and through which extends an operating rod of similar material. Fixed to one end of the rod is a stopper which, according to the relative position of the rod within the tube, may either open or close the corresponding end of the tube. Adjacent the other end of the tube is a cap through which the rod extends, and the cap has one or more air passages therein so as to enable the tube to be filled with fluid by thrusting its open end vertically through such fluid.

Due to the presence of the air passage or passages in the tube's cap, the contents of the tube could escape through such passages unless the tube is maintained constantly in a substantially vertical position with the cap uppermost. Since the maintenance of the tube in such position cannot be assured, a sampler according to the invention has a valve adjacent the capped end and which operates to seal the tube at a zone located between the air passages and the stoppered end. The sample thus is trapped between the stopper and the valve.

The operating rod is provided with an actuating handle which facilitates movements of the rod, the stopper, and the valve relative to the tube and which is adjustable to a position in which it positively maintains the stopper and the valve in sealing relation adjacent opposite ends of the tube.

DESCRIPTION OF THE DRAWINGS

A preferred embodiment of the invention is disclosed in the following description and in the accompanying drawings, in which:

FIG. 1 is a fragmentary, longitudinal sectional view of a sampling tube with the parts thereof in the positions they occupy when the tube is conditioned to take a sample;

FIG. 2 is a view similar to FIG. 1, but illustrating the parts of the apparatus in the positions they occupy when the tube contains a sample and the opposite ends of the tube are sealed; and FIGS. 3 and 4 are sectional views taken on the lines 3—3 and 4—4, respectively, of FIG. 2.

THE PREFERRED EMBODIMENT

The sampling apparatus constructed in accordance with a presently preferred form of the invention is designated generally by the reference character 1 and includes a cylindrical tube 2 formed of stainless steel, tetrafluoroethylene, or any other relatively inert, strong material which is resistant to breakage. The tube 2 preferably is of uniform diameter throughout its length and may be of any desired length, such as 1.5 meters, and have an inside diameter of about 4 centimeters.

Extending completely through the tube 2 is an elongate actuating rod 3 that is of considerably smaller diameter than that of the tube and which preferably is formed of stainless steel coated with heat shrinkable tetrafluoroethylene. One end 4 of the rod 3 preferably is threaded for the reception of a correspondingly threaded, conical stopper 5 formed of tetrafluoroethylene. The smaller end of the stopper has a diameter less than the inside diameter of the tube 2 and the larger end has a diameter greater than the inside diameter of the tube.

Adjacent the larger diameter end of the stopper is a frustoconical cavity 6 which forms an annular wall 7 that increases the flexibility of the larger diameter end of the stopper so as to enable the latter to be radially contracted as it enters the tube 2. The free end of the wall 7 is provided with a radially projecting flange 8 that may seat on the end of the tube.

Adjacent the opposite end of the tube is secured an externally threaded anchor ring 9 formed of stainless steel. A cap 10 of stainless steel has a correspondingly threaded skirt 11 which is threaded onto the ring 9. The skirt has a smooth bore 12 that terminates at one end in a shoulder 13 against which an annular valve seat 14 bears. The seat 14 is maintained in fixed position by the shoulder 13 and the end of the tube 2. The seat 14 is formed of a suitable material, such as tetrafluoroethylene, and has an opening 15 the diameter of which is greater than that of the rod 3 but less than that of a bore 16 that extends axially of the cap 10 and terminates at an end wall 17 provided with an opening 18 through which the rod 3 extends. The cap also has one or more radially extending passages 20 therein.

Fixed on the rod 3 by a tetrafluoroethylene pin 19 is a conical valve 21 formed of tetrafluoroethylene or the like. The valve has a conical wall 22 the smaller diameter end of which confronts the cap 10. The diameter of the smaller end of the valve 21 is less than that of the opening 15 in the valve seat 14, whereas the diameter of the larger end of the valve is greater than that of the opening 15.

That end 23 of the rod 3 which projects beyond the cap 10 is threaded for the accommodation of a correspondingly threaded fitting 24 of stainless steel or the like and to which an operating handle 25 of similar material is pivoted for movements between positions in which the handle lies athwart or parallel to the rod 3. The handle 25 is U-shaped in cross section and has parallel, spaced walls 26 joined by a web 27, the walls 26 straddling the fitting 24 and being pivoted to the latter by a stainless steel pin 28. The free edges 29 of the handle sides 26 are rounded.

The rod 3 is provided with an enlargement 30 between its free end and the cap 10, the enlargement limiting movement of the rod 3 to the right, as is viewed in FIGS. 1 and 2.

The outer face of the end wall 17 of the cap is provided with a circular recess 31 for a purpose which presently will be explained.

Means is provided for maintaining the tube 2 and the rod 3 coaxial and comprises one or more guide pins 32 of stainless steel or tetrafluoroethylene that are fixed to and extend transversely through the rod 3. The length of each pin corresponds substantially to the inside diameter of the tube 2 with sufficient clearance between the pin and the tube wall to enable free movement of the rod relative to the tube.

When the apparatus is conditioned for use, the handle 25 will be in the position shown in FIG. 1 and the rod 3 will have been moved through the tube 2 to disengage the stopper 5 from the end of the tube and to disengage the valve 21 from the seat 14. In these positions of the parts the sampler 1 may be held vertically, with the stopper 5 lowermost, and lowered into a drum or the like containing a fluid to be sampled. As the sampler 1 is lowered into the container, the fluid may enter the tube 2 through the lower end of the latter and air in the tube may be expelled through the passages 20. When the sampler has been lowered a desired distance, or when the stopper 5 engages the bottom of the container, the rod 3 may be moved relatively to the tube 2 (either by using the handle 25 or by pushing the stopper 5 against the bottom of the container) so as to cause the stopper to enter the lower end of the tube and seal the latter. Simultaneously, the valve 21 will enter the opening 15 in the annular seat 14 and seat on the latter so as to seal the opposite end of the tube.

Relative movement of the tube 2 and the rod 3 in such directions as to seal the opposite ends of the tube will result in displacement of the handle 25 in a direction away from the cap 10. When the opposite ends of the tube are sealed, the handle 25 may be rotated about the pivot pin 28 so that the longitudinal axis of the handle substantially parallels the longitudinal axis of the rod. This will cause one end or the other of the handle to bear upon the end wall 17 of the cap 10 with the end of the handle accommodated in the recess 31. The rounded edge 29 of the handle sides 26 facilitates seating of the handle in the recess 31. The other edges of the sides 26 are not rounded, thereby enabling the marginal edge of the recess 31 to function as a releasable latch to maintain the handle 25 in the position shown in FIG. 2 and in which the ends of the tube 2 are sealed. The relative positions of the handle 25 and the rod 3 may be adjusted by rotation of the fitting 24 on the rod. The clearance between the ends of the handle and the cap 10 thus may be adjusted to ensure a secure sealing of the ends of the tube 2 by the stopper and the valve.

As long as the ends of the tube are sealed by the stopper and the valve, the sampler 1 may be moved to any position without fear that its contents will be discharged inadvertently. Thus, the user of the sampler is protected against inadvertent leakage due to a nonvertical positioning of the sampler. Further, since the sampler is constructed of strong, durable materials, the risk of fracture of any of the parts thereof is minimized.

The disclosed embodiment is representative of a presently preferred form of the invention, but is intended to be illustrative rather than definitive thereof. The invention is defined in the claims.

I claim:

1. Sampling apparatus comprising an elongate tube open at both of its ends; an operating rod slideably accommodated in said tube and having a diameter less than that of said tube; a flexible, conical stopper fixed to one end of said rod for sliding movement with the latter from a first position beyond one end of said tube to a second position in sealing engagement with said one end of said tube, the smaller end of said stopper being of lesser diameter than the internal diameter of said tube and the larger end of said stopper being of greater diameter than the internal diameter of said tube; a valve seat seated on the other end of said tube, said valve seat having an opening therein through which said rod slideably passes; a flexible, conical valve fixed to said rod for sliding movements with the latter into and out of sealing engagement with said seat as said stopper moves into and out of sliding engagement with said one end of said tube, the smaller end of said valve being of lesser diameter than that of the opening in said seat and the larger end of said valve being of greater diameter than that of the opening in said seat, said seat and said valve together sealing said other end of said tube when said valve is in sealing engagement with said seat; and operating means carried by said rod outwardly of the other end of said tube for effecting simultaneous sliding movements of said rod, said stopper, and said valve relative to said tube.

2. Sampling apparatus according to claim 1 including guide means reacting between said rod and said tube for maintaining the longitudinal axes of said rod and said tube coaxial.

3. Sampling apparatus according to claim 1 including a cap at said other end of said tube through which said rod extends, said valve seat being located between said cap and said other end of said tube.

4. Sampling apparatus according to claim 1 including an air passage at said other end of said tube, said valve seat being located between said air passage and said one end of said tube.

5. Sampling apparatus according to claim 1 including a cap at said other end of said tube through which said rod extends, said cap having an air passage therein, said valve seat being located between said air passage and said one end of said tube.

6. Sampling apparatus according to claim 1 wherein said operating means comprises a handle pivoted to said rod for rocking movements relative thereto between a first position in which said handle extends athwart the longitudinal axis of said rod and a second position in which said handle substantially parallels such axis.

7. Sampling apparatus according to claim 6 including a cap at said other end of said tube, an end of said handle being engageable with said cap when said handle occupies said second position.

8. Sampling apparatus according to claim 7 wherein said cap has a recess therein for the accommodation of a part of said handle.

9. Sampling apparatus according to claim 7 wherein said cap has an air passage therein, said valve seat being between said air passage and said one end of said tube.

10. Sampling apparatus according to claim 1 wherein said larger end of said stopper has a recess therein forming an annular wall.

11. Sampling apparatus according to claim 10 wherein said recess is frustoconical.

12. Sampling apparatus according to claim 1 wherein said larger end of said stopper has a peripheral, radially extending flange for abutting said one end of said tube when said stopper is in sealing engagement with said one end of said tube.

13. Sampling apparatus comprising an elongate tube; an operating rod slideably accommodated in said tube and having a diameter less than that of said tube; a stopper fixed to one end of said rod for sliding movement with the latter into and out of sealing engagement with the corresponding end of said tube; a valve seat adjacent the other end of said tube; a valve carried by said rod for sliding movements with the latter into and out of sealing engagement with said seat as said stopper moves into and out of sealing engagement with said corresponding end of said tube; a cap at said other end of said tube; and an operating handle pivoted to said rod for effecting sliding movements thereof relative to said tube, said handle being rockable relative to said rod between a first position in which said handle extends athwart the longitudinal axis of said rod and a second position in which said handle substantially parallels such axis, said handle being engageable with said cap when said handle occupies said second position, and said cap having a recess therein for the accommodation of a part of said handle.

* * * * *